(12) United States Patent
Wang et al.

(10) Patent No.: US 11,972,443 B2
(45) Date of Patent: Apr. 30, 2024

(54) PREDICTION MODEL PREPARATION AND USE FOR SOCIOECONOMIC DATA AND MISSING VALUE PREDICTION

(71) Applicant: KONINKLIJKE PHILIPS N.V., Eindhoven (NL)

(72) Inventors: Xin Wang, Cambridge, MA (US); Eran Simhon, Boston, MA (US); Reza Sharifi Sedeh, Malden, MA (US); Amir Abdolahi, Malden, MA (US); Cecilia Meijer, Weston, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 383 days.

(21) Appl. No.: 16/772,425

(22) PCT Filed: Dec. 24, 2018

(86) PCT No.: PCT/EP2018/086840
§ 371 (c)(1),
(2) Date: Jun. 12, 2020

(87) PCT Pub. No.: WO2019/134873
PCT Pub. Date: Jul. 11, 2019

(65) Prior Publication Data
US 2021/0073629 A1 Mar. 11, 2021

Related U.S. Application Data

(60) Provisional application No. 62/612,829, filed on Jan. 2, 2018.

(51) Int. Cl.
*G06Q 30/00* (2023.01)
*G06Q 30/02* (2023.01)
*G06Q 30/0201* (2023.01)

(52) U.S. Cl.
CPC ......... *G06Q 30/02* (2013.01); *G06Q 30/0201* (2013.01)

(58) Field of Classification Search
CPC ............................................. G06Q 30/02–0277
See application file for complete search history.

(56) References Cited

U.S. PATENT DOCUMENTS

| 8,843,423 B2 | 9/2014 | Chu |
| 9,349,105 B2 | 5/2016 | Beymer |
| 2004/0186815 A1 | 9/2004 | Stockfisch |

FOREIGN PATENT DOCUMENTS

| WO | 2016179544 A1 | 11/2016 |
| WO | 2017083568 A1 | 5/2017 |

OTHER PUBLICATIONS

Mingo, Chivon A. et al "Individual and Community Socioeconomic Status: Impact on Mental Health in Individuals with Arthritis", Hindawi Puglishing Corporation, Arthiritis, vol. 2014, Article ID 256498, 10 pages, 2014.

(Continued)

*Primary Examiner* — Raquel Alvarez

(57) ABSTRACT

The present disclosure pertains to a system configured to prepare and use prediction models for socioeconomic data and missing value prediction. Some embodiments may: extract, from received population segment data, a training set of socioeconomic parameter values for each population segment; provide, to a prediction model as input, first parameter values of the respective training set for the prediction of additional parameter values of the training set such that the prediction of the additional parameter values is performed without reliance on the additional parameter values; provide, for each of the training sets, the additional parameter values to the prediction model as reference feedback for the prediction model's prediction of the additional parameter values to train the prediction model; and predict, (Continued)

based on a working set of parameter values for a population segment, additional values for the working set using the prediction model subsequent to its training.

20 Claims, 7 Drawing Sheets

(56) References Cited

OTHER PUBLICATIONS

Caro, Daniel H. et al "Measuring family socioeconomic status: An Illustration using data from PIRLS 2006", IERI Monograph Series, Issues and Methodologies in large-Scale Assessments vol. 5, 2012.
International Search report and Written Opinion of PCT/EP2018/086840, dated Apr. 30, 2019.
Kim, Han-Gyu et al "Recurrent Neural Networks with Missing Information Imputation for Medical Examination Data Prediction", BIGCOMP 2017.
Garcia-Laencina, Pedro J. et al "Pattern Classification with Missing data: a review", Neural Computer and Applications, vol. 19, 2010, pp. 263-282.
Wubetie, Habtamu Tilaye "Missing Data Management and Statistical Measurement of Socio-Economic Status: Application of Big Data", Journal of Big Data, vol. 4:47. 2017, pp. 1-44.

| Pop. segment | Median income | No. of households w/male householder (no wife present) | No. of households w/ at least one vehicle | ... | Parameter value n |
|---|---|---|---|---|---|
| A | 60816 | 384 | 674 | ... | ... |
| B | 86079 | (missing) | 812 | ... | ... |
| C | 76804 | 1191 | 751 | ... | ... |
| ... | ... | ... | ... | ... | ... |
| G | 104205 | 234 | 433 | ... | ... |

| Prediction models | Combinations of missing parameter values | Percentagev of population segments |
|---|---|---|
| Model 1a | Missing parameter values x and y | 10% |
| Model 1b | Missing parameter values x and n | 9% |
| Model 1c | Missing parameter values m, n, and o | 5% |
| . . . | . . . | . . . |

PREDICTION MODEL PREPARATION AND USE FOR SOCIOECONOMIC DATA AND MISSING VALUE PREDICTION

CROSS-REFERENCE TO PRIOR APPLICATIONS

This application is the U.S. National Phase application under 35 U.S.C. § 371 of International Application No. PCT/EP2018/086840, filed on Dec. 24, 2018, which claims the benefit of U.S. Provisional Patent Application No. 62/612,829, filed on Jan. 2, 2018. These applications are hereby incorporated by reference herein.

BACKGROUND

1. Field

The present disclosure pertains to a system configured to prepare and use prediction models for socioeconomic data (or other data) and missing value prediction.

2. Description of the Related Art

Prior data analytics have determined that disparities in health are not largely determined by biologic and genetic differences between people. Accountable care organizations (ACOS) attempting to accurately forecast healthcare needs of population segments thus have a need to use more relevant, available data. Socioeconomic data mined from public databases, though, may be erroneous and incomplete. Further, although it may be known in some instances to use models to make predictions that facilitate an improved, data-driven understanding of certain population segments, there remains much room for development of optimal training processes for these models.

SUMMARY

Accordingly, one or more aspects of the present disclosure relate to a system configured for computer-assisted preparation and use of prediction models. The system comprises one or more processors and/or other components. In some embodiments, the one or more processors are configured by machine-readable instructions to: receive, from one or more databases, population segment data related to population segments; extract, from the population segment data, a training set of parameter values for each of at least some of the population segments, wherein each parameter value of the training set of parameter values corresponds to a socioeconomic category; for each training set of the training sets of parameter values, provide one or more first parameter values of the training set to a prediction model as input for the prediction model to predict one or more additional parameter values of the training set such that the prediction of the one or more additional parameter values of the training set is performed by the prediction model without reliance on the one or more additional parameter values; for each training set of the training sets of parameter values, provide the one or more additional parameter values of the training set to the prediction model as reference feedback for the prediction model's prediction of the one or more additional parameter values to train the prediction model; and predict, based on one or more first parameter values of a set of parameter values for a population segment, one or more additional values for the set of parameter values using the prediction model subsequent to the training of the prediction model.

Yet another aspect of the present disclosure relates to a method for computer-assisted preparation and use of prediction models. The method is implemented by one or more hardware processors configured by machine-readable instructions and/or other components. In some embodiments, the method comprises: receiving, from one or more databases, population segment data related to population segments; extracting, from the population segment data, a training set of parameter values for each of at least some of the population segments, wherein each parameter value of the training set of parameter values corresponds to a socioeconomic category; for each training set of the training sets of parameter values, providing one or more first parameter values of the training set to a prediction model as input for the prediction model to predict one or more additional parameter values of the training set such that the prediction of the one or more additional parameter values of the training set is performed by the prediction model without reliance on the one or more additional parameter values; for each training set of the training sets of parameter values, providing the one or more additional parameter values of the training set to the prediction model as reference feedback for the prediction model's prediction of the one or more additional parameter values to train the prediction model; and predicting, based on one or more first parameter values of a set of parameter values for a population segment, one or more additional values for the set of parameter values using the prediction model subsequent to the training of the prediction model.

Still another aspect of the present disclosure relates to a system for computer-assisted preparation and use of prediction models. In some embodiments, the system comprises: means for receiving, from one or more databases, population segment data related to population segments; means for extracting, from the population segment data, a training set of parameter values for each of at least some of the population segments, wherein each parameter value of the training set of parameter values corresponds to a socioeconomic category; means for providing, for each training set of the training sets of parameter values, one or more first parameter values of the training set to a prediction model as input for the prediction model to predict one or more additional parameter values of the training set such that the prediction of the one or more additional parameter values of the training set is performed by the prediction model without reliance on the one or more additional parameter values; means for providing, for each training set of the training sets of parameter values, the one or more additional parameter values of the training set to the prediction model as reference feedback for the prediction model's prediction of the one or more additional parameter values to train the prediction model; and means for predicting, based on one or more first parameter values of a set of parameter values for a population segment, one or more additional values for the set of parameter values using the prediction model subsequent to the training of the prediction model.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
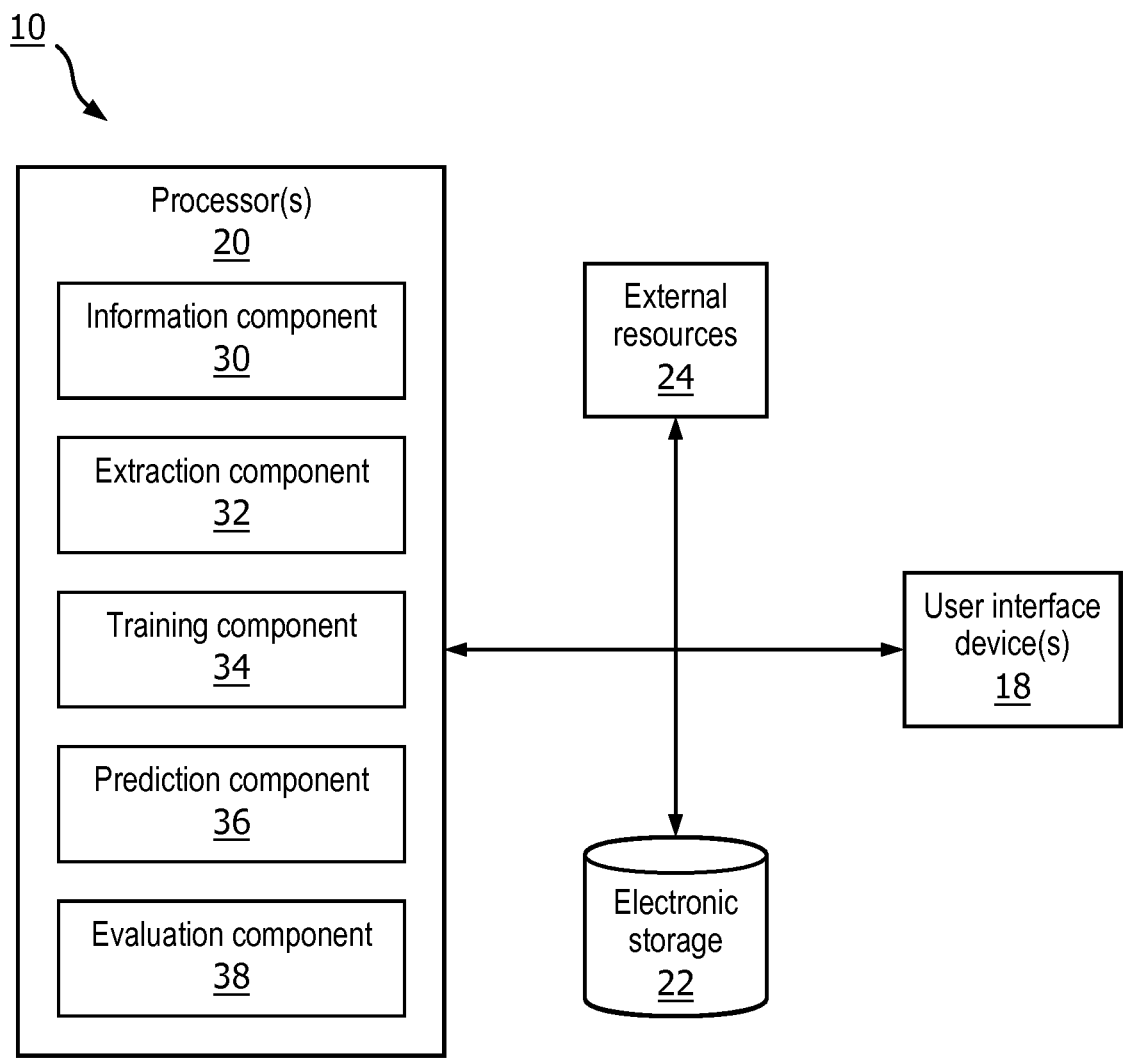
FIG. 1 is a schematic illustration of a system configured for preparing and using one or more prediction models for missing value prediction, in accordance with one or more embodiments.

As used herein, the singular form of "a", "an", and "the" include plural references unless the context clearly dictates otherwise. As used herein, the term "or" means "and/or" unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Training prediction models with known data improves accuracy and quality of outputs. Training data may be derived from any number of sources, such as census data or health information providers, and the data may pertain to any number of population segments. A population segment may be one or more persons of a particular geographic region, census unit, tract, county, zip code, group, family, demography, community, neighborhood, city, state, province, county, country, group of countries, or other type of population segment. Subsequent data analysis may then better understand determinants leading to disparities in statuses or outcomes associated with the population segments. Accurate characterizations of the socioeconomic statuses of population segments, for example, helps to optimize deployment of healthcare resources to subsequently improve healthcare outcomes. That is, where healthcare outcomes of a population segment are at unacceptable levels, then healthcare services may be triggered to improve the outcomes for that population segment. As a result, utilization for primary care, general hospital care, or tertiary care may be eventually decreased.

Trained models may be used to predict the status (e.g., socioeconomic, fiscal, personal, sociological, medical, demographical, or other type of status) of a population segment and to understand how certain determinants (e.g., socioeconomic, fiscal, personal, sociological, educational, transportation availability, medical, demographical, or other type of determinant) impact an outcome (e.g., health, financial, societal, professional, educational, or other type of outcome) of the population segment. Properly trained prediction models may thus generate new data that facilitates better understanding of the known (and unknown) data. For example, prediction models may determine status trends for population segments using longitudinal data. The training of these models, though, is a non-trivial task.

FIG. 1 illustrates a system 10 configured to prepare and use one or more prediction models, for missing value prediction, in accordance with one or more embodiments. System 10 may be configured to receive population segment data (e.g., incomplete data) or other data, extract relevant portions of the data, and train models that can predict useful values. As an example, the prediction models may learn or adjust weights (to be applied to data) and generate predictions based on such weights. As another example, the prediction models may be configured to predict additional, missing, or other data (e.g., based on the learned/adjusted weights or other criteria).

The prediction models may be and/or include one or more neural networks (e.g., deep neural networks, artificial neural networks, or other neural networks), other machine learning models, or other prediction models. As an example, the neural networks referred to variously herein may be based on a large collection of neural units (or artificial neurons). Neural networks may loosely mimic the manner in which a biological brain works (e.g., via large clusters of biological neurons connected by axons). Each neural unit of a neural network may be connected with many other neural units of the neural network. Such connections may be enforcing or inhibitory, in their effect on the activation state of connected neural units. These neural network systems may be selflearning and trained, rather than explicitly programmed, and can perform significantly better in certain areas of problem solving, as compared to traditional computer programs. In some embodiments, neural networks may include multiple layers (e.g., where a signal path traverses from front layers to back layers). In some embodiments, back propagation techniques may be utilized by the neural networks, where forward stimulation is used to reset weights on the "front" neural units. In some embodiments, stimulation and inhibition for neural networks may be more free-flowing, with connections interacting in a more chaotic and complex fashion. As another example, the prediction models may be and/or include one or more recurrent neural networks, multiresolution recurrent neural networks, logistic regression, generalized linear models, Hidden Markov Models, rule-based models, probabilistic models, and/or other prediction models.

In some embodiments, system 10 facilitates an understanding of disparities in outcomes between different population segments, before, after, or without performing missing data imputation. Data imputation is a statistical approach to replace missing, erroneous, or otherwise untrustworthy data with substituted values. The substituted values may be predicted with one or more prediction models.

In some embodiments, system 10 quantifies a status (e.g., socioeconomic status) of a population segment using population segment data (e.g., census data, outcome information, and/or any other data that describes the population segments). Population segments may each have a set of parameter values that are associated with or that describe the respective population segment. In some use cases, one or more parameter values of one or more sets of one or more population segments may be missing. For example, the parameter value informing the number of households with a male householder (and no wife present) may be missing in 10% of the data associated with a group of population segments.

In some embodiments, system 10 comprises one or more user interface devices 18, one or more processors 20, electronic storage 22, external resources 24, and/or other components. As shown in FIG. 1, system 10 may provide interfaces to and from external resources 24, electronic storage 22, or one or more other databases. System 10 may have access to information from websites and to database information, such as parameter values describing population segments and/or health outcome information. For example, system 10 may access census data of any geographic area, a hospital information system (HIS), a clinical data repository (CDR), electronic medical records (EMRs), and/or any other source of information. The collected information may include parameter values of one or more categories, health data, or other information (e.g., demographic, background, etc.), with respect to one or more population segments.

Electronic storage 22 of FIG. 1 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may be (in whole or in part) a separate component within system 10, or electronic storage 22 may be provided (in whole or in part) integrally with one or more other components of system 10 (e.g., a user interface device 18, processor 20, etc.). In some embodiments, electronic storage 22 may be located in a server together with processor 20, in a server that is part of external resources 24, in user interface devices 18, and/or in other locations. Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 22 may store software algorithms, information obtained and/or determined by processor 20, information received via user interface devices 18 and/or other external computing systems, information received from external resources 24, and/or other information that enables system 10 to function as described herein.

External resources 24 include sources of information (e.g., databases, websites, etc.), external entities participating with system 10 (e.g., a medical records system that stores patient census information and a population records system that stores resident census information), one or more servers outside of system 10, a network (e.g., the Internet), electronic storage, equipment related to Wi-Fi technology, equipment related to Bluetooth® technology, data entry devices, and/or other resources. In some implementations, some or all of the functionality attributed herein to external resources 24 may be provided by resources included in system 10. External resources 24 may be configured to communicate with processor 20, user interface device 18, electronic storage 22, and/or other components of system 10 via wired and/or wireless connections, via a network (e.g., a local area network and/or the Internet), via cellular technology, via Wi-Fi technology, and/or via other resources.

User interface device(s) 18 of system 10 may be configured to provide an interface between one or more users and system 10. User interface devices 18 are configured to provide information to and/or receive information from the one or more users. User interface devices 18 include a user interface and/or other components. The user interface may be and/or include a graphical user interface configured to present views and/or fields configured to receive entry and/or selection with respect to particular functionality of system 10, and/or provide and/or receive other information. In some embodiments, the user interface of user interface devices 18 may include a plurality of separate interfaces associated with processors 20 and/or other components of system 10.

In some embodiments, user interface devices 18 are configured to provide a user interface, processing capabilities, databases, and/or electronic storage to system 10. As such, user interface devices 18 may include processors 20, electronic storage 22, external resources 24, and/or other components of system 10. In some embodiments, user interface devices 18 are connected to a network (e.g., the Internet). In some embodiments, user interface devices 18 do not include processor 20, electronic storage 22, external resources 24, and/or other components of system 10, but instead communicate with these components via dedicated lines, a bus, a switch, network, or other communication means. The communication may be wireless or wired. In some embodiments, user interface devices 18 are laptops, desktop computers, smartphones, tablet computers, and/or other user interface devices.

Examples of interface devices suitable for inclusion in user interface device 18 include a touch screen, a keypad, touch sensitive and/or physical buttons, switches, a keyboard, knobs, levers, a display, speakers, a microphone, an indicator light, an audible alarm, a printer, and/or other interface devices. The present disclosure also contemplates that user interface devices 18 include a removable storage interface. In this example, information may be loaded into user interface devices 18 from removable storage (e.g., a smart card, a flash drive, a removable disk) that enables users to customize the implementation of user interface devices 18.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., a server), or processor 20 may represent processing functionality of a plurality of devices operating in coordination (e.g., one or more servers, user interface devices 18, devices that are part of external resources 24, electronic storage 22, and/or other devices).

In some embodiments, processor 20, external resources 24, user interface devices 18, electronic storage 22, and/or other components may be operatively linked via one or more electronic communication links. For example, such electronic communication links may be established, at least in part, via a network such as the Internet, and/or other networks. It will be appreciated that this is not intended to be limiting, and that the scope of this disclosure includes embodiments in which these components may be operatively linked via some other communication media. In some embodiments, processor 20 is configured to communicate with external resources 24, user interface devices 18, electronic storage 22, and/or other components according to a client/server architecture, a peer-to-peer architecture, and/or other architectures.

As shown in FIG. 1, processor 20 is configured via machine-readable instructions to execute one or more computer program components. The computer program components may comprise one or more of information component 30, extraction component 32, training component 34, prediction component 36, evaluation component 38, and/or other components. Processor 20 may be configured to execute components 30, 32, 34, 36, and/or 38 by software; hardware; firmware; some combination of software, hardware, and/or firmware; and/or other mechanisms for configuring processing capabilities on processor 20.

It should be appreciated that although components 30, 32, 34, 36, and 38 are illustrated in FIG. 1 as being co-located within a single processing unit, in embodiments in which processor 20 comprises multiple processing units, one or more of components 30, 32, 34, 36, and/or 38 may be located remotely from the other components. The description of the functionality provided by the different components 30, 32, 34, 36, and/or 38 described below is for illustrative purposes, and is not intended to be limiting, as any of components 30, 32, 34, 36, and/or 38 may provide more or less functionality than is described. For example, one or more of components 30, 32, 34, 36, and/or 38 may be eliminated, and some or all of its functionality may be provided by other components 30, 32, 34, 36, and/or 38. As another example, processor 20 may be configured to execute one or more additional components that may perform some or all of the functionality attributed below to one of components 30, 32, 34, 36, and/or 38.

In some embodiments, information component 30 is configured to receive population segment data from electronic storage 22, external resources 24, and/or user interface device(s) 18. The population segment data may include sets of parameter values and/or outcomes. In some embodiments, information component 30 is configured to aggregate information from various sources (e.g., external resources 24, electronic storage 22, user interface device(s) 18, or other source(s)). In some embodiments, information component 30 is configured to provide altered sets of parameter values and/or calculated outcomes (and/or determined statuses) to electronic storage 22, external resources 24, and/or user interface device(s) 18. Information component 30 may access via a communications interface one or more devices included in external resources 24 and/or other devices. In some embodiments, information component 30 includes a plurality of separate interfaces (e.g., a communications interface). In some embodiments, information component 30 is connected to a network (e.g., the Internet). The connection to the network may be wireless or wired. In some embodiments, information component 30 may, via electronic storage 22, external resources 24, and/or user interface device(s) 18, receive and/or provide the parameter values and/or the outcomes through different interfaces, such as serial (e.g., RS-232), optical link, RF link, an IR link, a communications bus, a modem (telephone, cable, etc.), and/or other communication interfaces.

In some embodiments, information component 30 may instigate the retrieval of available (e.g., public, private, or some combination of public and private) sets of parameter values and outcomes. For example, information component 30 may instigate the reading or downloading of data from cloud storage, one or more databases, or one or more websites. In some embodiments, information component 30 may receive the sets of parameter values and the outcomes from one or more databases. The databases used for retrieving the parameter values may be the same as or different from the databases used for retrieving the outcomes.

The databases serving parameter values may be associated with a census bureau or any other publicly available database. In embodiments where the parameter values are received as part of census data (or in other embodiments), the parameter values may be in any category, such as income, population size, education level, employment status, health insurance status, occupation, household type, family size, percentage of people below the poverty line, or another category. The databases serving outcomes (e.g., healthcare outcomes) may be associated with the American Community Survey (ACS), Johns Hopkins' index, or any other accessible database.

In some embodiments, information component 30 is configured to obtain parameter values, outcomes, and/or other information. The parameter values and the outcome information may be associated with one or more population segments. That is, in some embodiments, each set of the parameter values is associated with one population segment. Similarly, in some embodiments, each outcome is associated with one population segment.

As mentioned, the parameter values may describe the population segments fiscally, socioeconomically, personally, sociologically, medically, or by any other description. Each of the outcomes may be related to a particular type of health information, such as healthcare metrics with respect to the population segments. For example, each of the obtained healthcare outcomes may describe an average (e.g., mean, median, mode, etc.) of the population segment's life expectancy, body-mass index (BMI) statistics, hospital readmission rate, total Emergency department visits, healthcare costs, healthcare utilization rates, percentage of population with diabetes (e.g., by blood glucose A1C level), or another healthcare outcome. Life expectancy data for various population segments may be obtained for one or more time periods (e.g., from 1980 to present day or other time periods) from one or more sources (e.g., from websites via one or more web crawling/scraping techniques, from one or more databases, etc.).

In some embodiments, information component 30 may store the received data in a third-party cloud storage (e.g., iCloud, Amazon Web Service, or another cloud storage), with respect to an in-house data analytics platform, and/or at electronic storage 22.

Figures 2, 3:
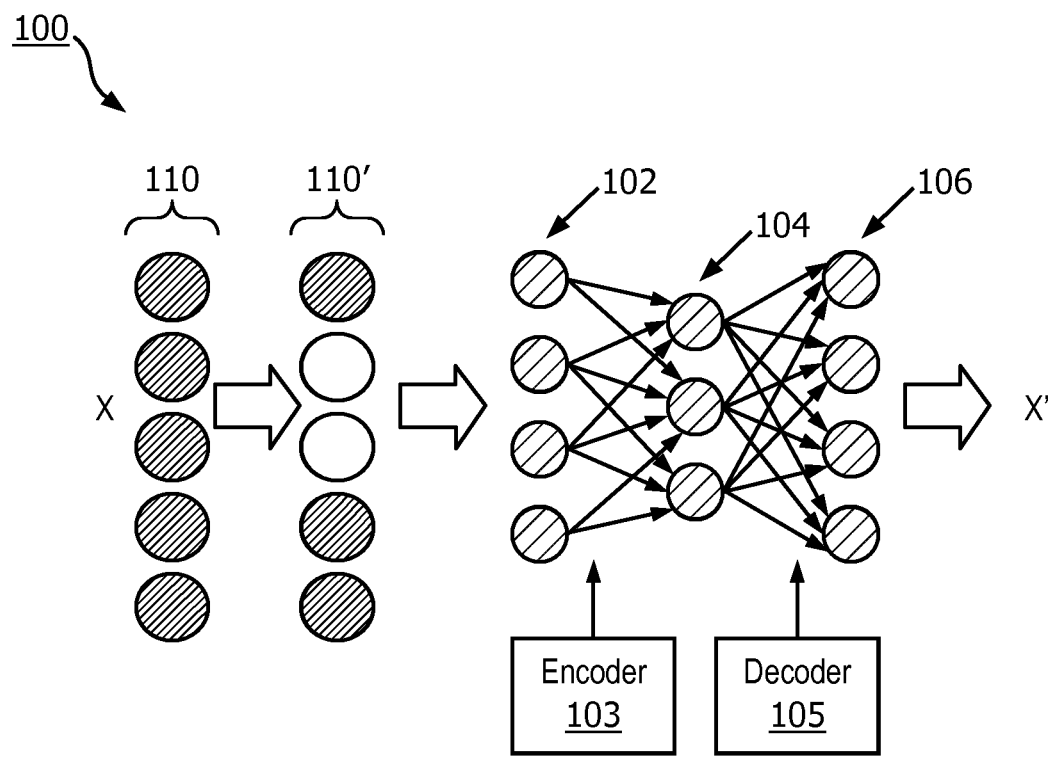
FIG. 2 illustrates an exemplary database table listing parameter values for a plurality of population segments, in accordance with one or more embodiments.
FIG. 3 illustrates the training of a prediction model, in accordance with one or more embodiments.

FIG. 2 depicts some received parameter values in one exemplary use case, in accordance with one or more embodiments. This example is not intended to be limiting, as any number of population segments and any number of parameter values in any type of category and format are contemplated herein. In this example of FIG. 2, information component 30 may participate in the reception and storage of a set of parameter values for each of the A, B, C, . . . and G population segments. Further, the each set of parameter values includes n number of parameter values in distinct categories. This exemplary set includes median income, number of households with a male householder present (and no wife), number of households with at least one vehicle, and at least parameter value n, which may be any category.

The table depicted in FIG. 2 lists exemplary values of a set of parameter values in different categories, the values being associated with particular population segments for a particular time period. In some instances, as shown in FIG. 2, some parameter values may be missing, as compared with the parameter values of other population segments. More specifically, in this example, the number of households with a male householder (and no wife present) may be in the received population segment data for population segments A, C, and G but not for population segment B. That is, at least population segments A, C, and G may have no missing parameter values, when compared with population segment B, which at least lacks one value for the second listed parameter, as shown.

In some embodiments, extraction component 32 is configured to extract parameter values and/or outcomes from data received via information component 30. In some embodiments, the received data may be the population segment data. The received data may be in any format. For example, extraction component 32 may extract the parameter values and the outcome information from text, tables, graphs, charts, spreadsheets, and/or other computer readable formats (e.g., binary, hexadecimal, or other format).

In some embodiments, extraction component 32 implements quality control before or after extracting the data. For example, extraction component 32 may apply quality control to the received parameter values such that some parameter values for some population segments are removed. In this example, each of the some parameter values may be removed from the some population segments based on a determined confidence value (e.g., margin of error, reliability of the data, etc.) of the some parameter value breaching a predetermined threshold. In some embodiments, extraction component 32 extracts data from the received population segment data such that it is immediately usable by one or more prediction models.

In some embodiments, training component 34 is configured to train one or more machine learning prediction models. The prediction models of training component 34 may be trained based on the extracted sets of parameter values, outcome information, and/or other information. For example, training component 34 may train a prediction model using one or more training sets of parameter values. In another example, training component 34 may train a prediction model using one or more outcomes and sets of parameter values.

In some embodiments, training component 34 may train a prediction model to predict additional parameter values. Training component 34 may, in some embodiments, use neural networks to capture the highly nonlinear correlations between a plurality of parameter value sets of a plurality of population segments.

FIG. 3 illustrates an example of how a neural network (e.g., prediction model 100) may be trained. A prediction model of system 10 (FIG. 1) may be used, in accordance with one or more embodiments. Untrained prediction model 100 may include an input layer 102, one or more other layers 104 (e.g., a hidden layer), and an output layer 106, as shown in FIG. 3. The number of layers is not intended to be limiting. Each circular node of layers 102, 104, and 106 represents an artificial neuron that may perform calculations using one or more parameters, and the various interconnecting lines are arrows representing connections from the output of one neuron to the input of another. The output x' of model 100 may be one or more parameter values or a set of parameter values.

In some embodiments, prediction model 100 is a deep neural network, including encoder 103 and decoder 105. The training process implemented by training component 34 may comprise removal of one or more known parameter values from a training set of parameter values. In doing so, model 100 may attempt reconstruction of the original (i.e., removed) parameter value(s) by predicting one or more additional values. Each of the original parameter values is represented in FIG. 3 as a circular node in sets 110 and 110'. A shaded node of sets 110 and 110' represents a known parameter value, and an unshaded node of set 110' represents a removed parameter value. As such, the input x to untrained prediction model 100 may be a training set of parameter values 110, which may be previously extracted from the received population segment data.

In some embodiments, training component 34 (FIG. 1) may be configured such that inputs to a prediction model (e.g., model 100) are represented as feature vectors. That is, training set 110 may be a feature vector, where each dimension of the vector pertains to a different parameter value category.

In some embodiments, training component 34 may enable one or more prediction models to be trained. Training data used to train the prediction models may include (i) inputs to be provided to a prediction model, (ii) reference outputs that are to be derived from a prediction model's processing of such inputs, (iii) reference indications of outputs that are not to be derived from a machine learning model's processing of such inputs, or (iv) other training data.

FIG. 3 illustrates the training process beginning by input training set 110 being operated on by training component 34. That is, training component 34 may initially select one or more parameter values from one or more input training sets. That is, in the example of FIG. 3, two parameter values of the five available in input training set 110 are intentionally removed, arriving thus at altered training set 110'. Input layer 102 then receives incomplete training set 110' such that model 100 outputs x', output x' being one or more parameter values or one or more sets of parameter values. To predict x', model 100 performs calculations at layers 102, 104 and/or 106 (which operate with respect to encoder 103 and decoder 104). Model 100 may use some or all of the known parameter values of training set 110 to predict x' such that x' approximates the removed parameter values.

Training component 34 may cause one or more prediction models to generate predictions. For example, a prediction model may analyze its predictions against a set of reference feedback, such as reference predictions of parameter values. In some use cases, the reference outputs may be provided as input to the prediction models (e.g., prior to, simultaneously with, or subsequent to providing parameter values to the prediction model), which the prediction model may utilize to determine whether its predictions are accurate, determine the level of accuracy or completeness with respect to each prediction, or make other determinations (e.g., via deep learning through its multiple layers of abstraction or other techniques). Such determinations may be utilized by the prediction models to improve the accuracy or completeness of their predictions. In another use case, accuracy or completeness indications with respect to the prediction models' predictions (e.g., whether a given prediction is accurate, how accurate or complete a given prediction is, etc.) may be provided to the prediction model, which, in turn, may utilize the accuracy or completeness indications to improve the accuracy or completeness of its predictions.

Training component 34 may, in some embodiments, use a mean squared error (MSE) algorithm as a loss function. For example, model 100 may attempt one or more predictions of x' until a difference (i.e., error) between x and x' is minimized. Such minimization may be performed via the MSE algorithm, input x being one or more parameter values or one or more training sets of parameter values. The MSE algorithm may thus be used to minimize the square of the difference between input x and output x' and, in doing so, trains the prediction model. That is, the MSE algorithm may minimize one or more differences between one or more additional parameter values provided as reference feedback and a prediction of the additional parameter values. As such, if the same or different parameter value(s) of a set (e.g., set 110 or another set) were to be input as reference feedback into model 100 for its training, the model may make a prediction that is closer to the original or removed (known) parameter value(s). In other words, known input x may serve as reference feedback such that model 100's output x' approximates the input.

Figures 4, 5:
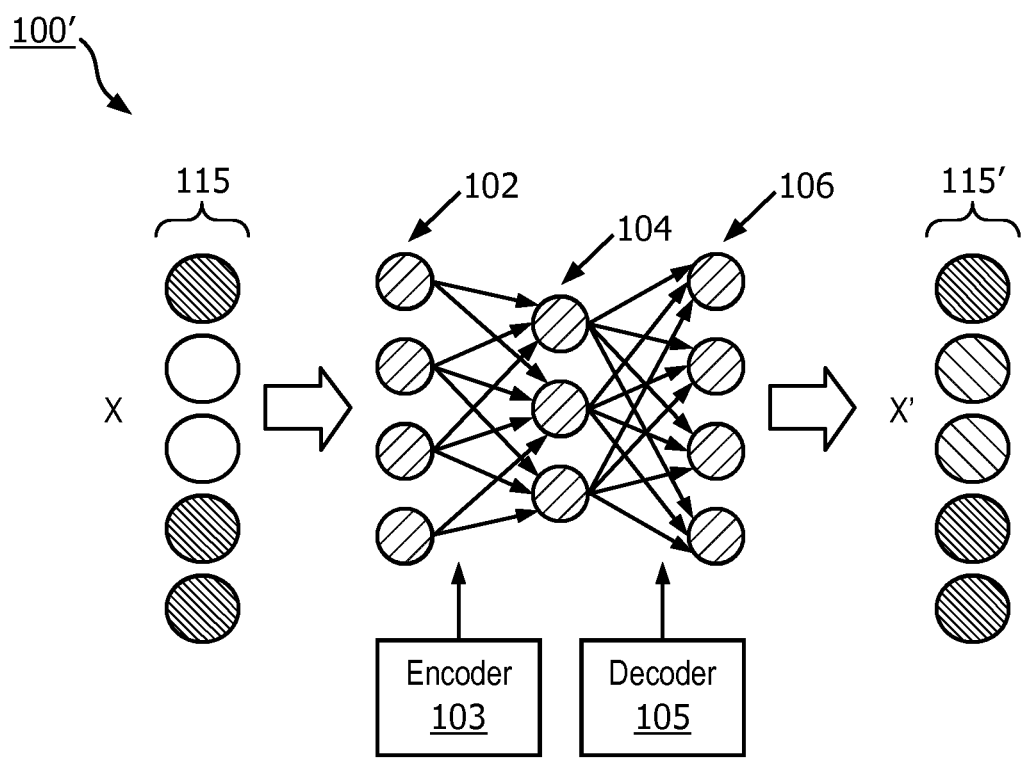
FIG. 4 illustrates a table for an exemplary scenario with respect to a group of population segments where certain parameter values are missing for some of the population segments, in accordance with one or more embodiments.
FIG. 5 illustrates a trained prediction model predicting parameter values for a working set of parameter values of a particular population segment that has some parameter values missing, in accordance with one or more embodiments.

FIG. 4 illustrates a table for an exemplary scenario with respect to a group of population segments, in accordance with one or more embodiments. Specifically, FIG. 4 depicts certain parameter values that are missing for some of the population segments. More particularly, the figure shows that training component 34 may train some, different prediction models (e.g., models 1a, 1b, and 1c) to account for the exemplary scenario in which three different patterns of missing parameter values are identified, each pattern being identified with respect to a percentage of population segments that do not have that pattern of parameter values in their working set of parameter values. In this example: (i) 10% of the population segments of the group do not have a value (e.g., missing, incorrect, unreliable, or otherwise unknown value) for each of parameters x and y (a first pattern), x and y representing values of any parameter category; (ii) 9% of the population segments do not have a value for each of parameters x and n (a second pattern), n representing a value of any (e.g., different) parameter category; and (iii) 5% of the population segments do not have a value for each of parameters m, n, and o (a third pattern), m and o representing values of any (e.g., different) parameter categories. But these exemplary values and variable parameters of FIG. 4 are not intended to be limiting, since training component 34 may train any number of prediction models to predict any number or pattern of parameter values and any percentage of population segments may be resolvable by the prediction models. For example, training component 34 may train prediction models with, e.g., 2 or more, 5 or more, 10 or more, 100 or more, 1000 or more, 10000 or more, or other numbers of parameter values.

In some embodiments, training component 34 trains one or more models, each of which being for an individual combination or pattern of parameter values. If a certain percentage (e.g., 10%, as shown in FIG. 4) of the population segments do not have values for parameter x and y, training component 34 can train one prediction model (e.g., model 1a) for predicting values in the same categories as parameters x and y, for each of these certain population segments. Similarly, if a certain percentage (e.g., 9%, as shown in FIG. 4) of the population segments do not have values for the parameters x and n, training component 34 may train another prediction model (e.g., model 1b) for predicting parameter values for these other population segments.

In some embodiments, training component 34 may train one or more other prediction models. For example, training component 34 may train a prediction model such that it is operable to quantify outcomes and socioeconomic statuses of population segments, where each of the statuses is evaluated by one or more of the outcomes. In some embodiments, the prediction model is one or more regression models. For example, training component 34 may use predictor and response variables to train a regression model. For example, training component 34 may use the outcomes extracted by extraction component 32 for the training. In some embodiments, training component 34 may train the prediction model by using the extracted (or predicted) parameter values of some set(s) as independent (e.g., predictor) variables and the extracted outcomes as the dependent (e.g., response) variable.

In some embodiments, training component 34 may use an extracted outcome associated with a population segment as a response variable, then the regression model may be trained via an equation similar to Equation 1, below, where Y is the extracted outcome, $X_i$ are the parameter values of a set, and $W_i$ are the weights (coefficients) associated with the parameter values of the set. The prediction model may, via its training, learn or solve for each of the weights/coefficients $W_i$. In these examples, index i may be the number of parameter values in a training or working set of parameter values.

$$Y_{life\_expectancy} = W_1 X_{income} + W_2 X_{education} + \ldots \qquad [\text{Eq. 1}]$$

In some embodiments, training component 34 may use any number of outcomes to train the prediction model. In exemplary Eq. 1, one outcome (life expectancy) is used for the training.

In some embodiments, prediction component 36 causes the trained neural networks of one or more prediction models to output neural network responses. In some embodiments, prediction component 36 may predict additional parameter values using the prediction model. In some embodiments, prediction component 36 utilizes one or more of a plurality of data prediction (e.g., statistical imputation) methods to impute missing or additional data. For example, prediction component 36 may use hot-deck (i.e., matching) imputation, cold-deck imputation, mean substitution, regression (e.g., random, iterative, etc.), routine multivariate, multiple imputation, model-based, or one or more other data imputation methods.

In some embodiments, prediction component 36 may predict the additional or missing parameters using the K-nearest neighbors algorithm. For implementing aspects of this algorithm, prediction component 36 may compute a similarity between one or more population segments of a group and a plurality of other population segments of the group based on the sets of extracted parameter values for these population segments. In some embodiments, prediction component 36 uses a deep learning based method to capture nonlinear correlations between several parameter values of the plurality of population segments to predict additional values for the population segments. The population segments may have missing, from their respective working set of parameter values, some parameter values or require additional parameter values.

Prediction component 36 may analyze the computed or captured similarities between similar population segments to choose K nearest neighbors of the population segments, K being an integer. For example, three population segments may be identified as having similar parameter values. In this example, prediction component 36 may determine the three nearest neighbors to have similar population segments based on feature vectors representing each of these population segments; each of the feature vectors may be based on a training set or working set of the respective population segment. In this example, if one of these three population segments is missing or requiring a parameter value (e.g., transportation availability), but the other two population segments do have values for that parameter, then prediction component 36 may predict this parameter value for the one population segment based on the values of the parameters of the other two population segments. In particular, prediction component 36 may use an average value (e.g., mean, mode, median, etc.) of the parameter values of these two nearest neighboring population segments to predict the missing/additional parameter value for the one population segment. That is, in some use cases, prediction model 36 may predict the missing/additional parameter value to impute parameter values that the one population segment may be missing by comparison with the nearest neighboring population segments. However, prediction component 36, may not be able to accurately choose the nearest neighbors, if the number of parameter values in the respective sets is too large.

In some embodiments, prediction component 36 may apply a model (e.g., exemplary, trained prediction model 100') to particular population segments requiring additional or lacking reliable parameter values. FIG. 5 illustrates exemplary, trained prediction model 100' in a process of predicting one or more parameter values. A shaded node of sets 115 and 115' may represent a known parameter value, and an unshaded node of set 115 represents a missing, incorrect, unreliable, or otherwise unknown parameter value for which the prediction model attempts prediction. For example, the unshaded node may be the missing number of households with a male householder of population segment B, as shown in FIG. 2.

In some use cases, prediction component 36 may output, via model 100', a prediction, the prediction being one or more parameter values. In the example of FIG. 5, two parameter values may be required or are missing from working set 115. Working set 115 may have five parameter values, but only three of them (as shown shaded in FIG. 5) are currently known. In the example of FIG. 5, trained model 100' accurately predicts two parameter values for set 115' in similar or the same categories as the two removed parameter values, which are shown removed from altered training set 110' in FIG. 3. This is because untrained model 100 may be exemplarily trained to be trained model 100' using a same or similar pattern of parameter values. Resulting from the prediction, trained model 100' may output completed, working set 115', which includes two predicted parameter values. Model 100' may be trained to predict any pattern of missing/additional parameter values. For example, the two hatched circles of set 115' in FIG. 5 represent missing parameter values that were predicted by the trained prediction model 100'. In some embodiments, the predicted parameter values may not complete working set 115, since working set 115 may still have missing or otherwise require prediction of other parameter value(s).

In some embodiments, prediction component 36 may, via the trained prediction model, calculate outcomes for the population segments. For example, a prediction model of prediction component 36 may use extracted and/or predicted parameter values and their respective trained weights to calculate a new or otherwise unknown outcome. For example, the trained prediction model may predict one or more outcomes for one or more population segments.

Further, with the prediction model, prediction component 36 may facilitate analysis as to how the parameter values impact the outcome. For example, the prediction model may facilitate analysis as to how socioeconomic parameter values impact healthcare outcomes. Still further, with the prediction model, prediction component 36 may use an extracted or predicted outcome to determine a status for each of a plurality of population segments of a group. The population segment statuses may, in some embodiments, be a normalized representation of the outcomes, the normalization being with respect to the other population segments of the group.

In some embodiments, prediction component 36 may use the outcomes predicted by the prediction model and/or the extracted outcomes as longitudinal data to train a machine learning model to predict future outcomes, the predicted outcomes being used to calculate future statuses. For example, based on the status determined for a population segment via a prediction model, prediction component 36 may predict the status for the population segment in a future time period (e.g., in 5, 10, or 15 years or any other future time period).

In some embodiments, prediction component 36 may be configured to use another prediction model (e.g., a recurrent neural network (RNN)) to calculate and predict statuses over sequential time periods. Use of the other prediction model, which may use the longitudinal data, is exemplarily illustrated in FIG. 6. For example, year 0 could be 2001, year 5 could be 2006, year 10 could be 2011, and year 15 could be 2016. By inputting a set of parameter values and the calculated status $n_{10}$ into the prediction model for population segment n, prediction component 36 may predict the status for year 15. The prediction model may be trained using one or more sets of parameter values and one or more statuses associated with each of at least one population segment.

Figure 6:
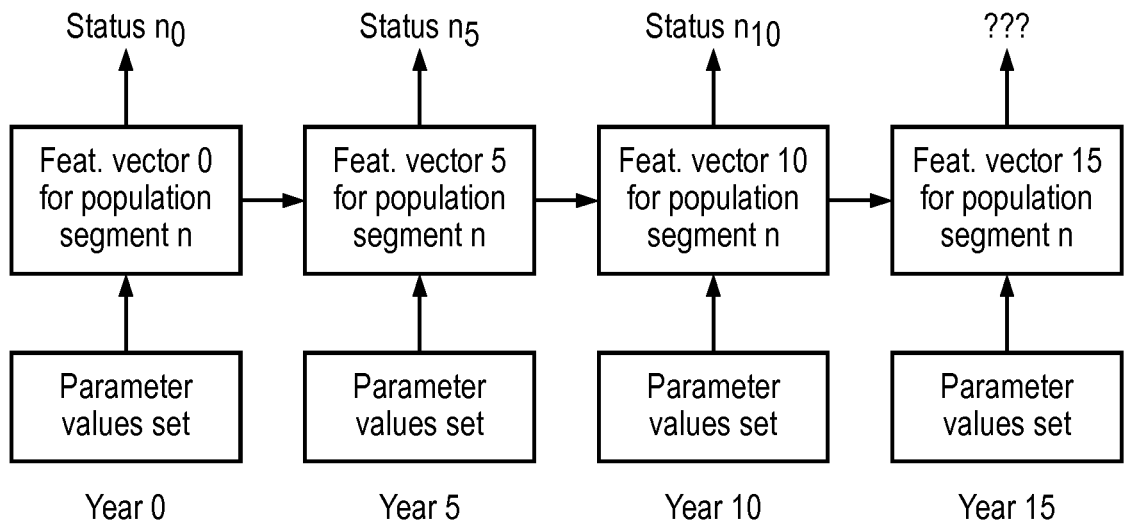
FIG. 6 illustrates a prediction model for predicting a trending status for a particular population segment, in accordance with one or more embodiments.

FIG. 6 depicts use of an exemplary RNN for predicting status of a population segment using training data. In the example of FIG. 6, the training data may be sets of parameter values of current, previous, or future time periods. The input set of parameter values may be aggregated, for a population segment, into a feature vector that describes the population segment. In some embodiments, each of the feature vectors may have as many dimensions as there are parameter values in the set. While one prediction model may be configured to predict an outcome based on a combination of parameter values and associated weights, another prediction model may use such outcome and one or more parameters of the feature vector to predict the status for a particular time frame. For example, using the parameter values set for year 0 prediction component 36 may generate status $n_0$. Similarly, prediction component 36 may iterate through one or more other years' data to calculate other statuses (e.g., statuses $n_5$ and $n_{10}$ for years 5 and 10, respectively). With these other statuses known and using the feature vector for population segment n at year 15, prediction component 36 may predict the additional status of year 15, which is depicted as ??? in FIG. 6.

In some embodiments, the prediction models of prediction component 36 may be and/or include one or more neutral networks that are trained and utilized for generating outputs (as described herein). In some embodiments, each connection (or the neutral unit itself) may have a threshold function such that the signal must surpass the threshold before it is allowed to propagate to other neural units. In some embodiments, system 10 comprises a deep neural network powered prediction component. In some embodiments, prediction component 36 may be powered additionally or alternatively by one or more other types of neural networks or other types of prediction models.

In some embodiments, prediction component 36 uses the deep learning method (e.g., data structured learning, hierarchical learning, etc.) to predict additional data. The additional data may be outcomes, and the outcomes may be used in some instances to facilitate calculation of the statuses for population segments.

In some embodiments, evaluation component 38 may rescale or normalize each of the calculated outcomes (e.g., into a scale of 1 to 5, 1 to 10, 1 to 100, or any other suitable range), as a quantification of an overall status. In some embodiments, evaluation component 38 may calculate a status for each of a plurality of population segments using a prediction model discussed above (e.g., a machine learning model). Each population segment may be determined to have a status value, for example, a socioeconomic status. The higher the value is, the better the particular population segment's status may be. But this is not intended to be limiting, as lower values may be deemed better in other use cases. The status value may be based on an extracted outcome, a predicted outcome (e.g., using the prediction model), or on another value.

In some embodiments, after a healthcare outcome for some population segment is calculated using the prediction model and after a socioeconomic status is determined based on the calculated healthcare outcome for the population segment, evaluation component 38 may prepare performance of a healthcare service for one or more members of the population segment, if the determined socioeconomic status breaches a predetermined threshold.

Evaluation component 38 may provide to user interface device 18 the determined statuses such that a distribution (e.g., a heat map) of these statuses is displayed to an interested user. The display may be similar to that showed in the example of FIG. 7B. In some embodiments, evaluation component 38 may provide to user interface device 18 the learned weights (coefficients) of the prediction model, as exemplarily depicted in FIG. 7A. In some embodiments, evaluation component 38 may provide to user interface device 18 a representation (e.g., a chart) of the current statuses and predicted statuses for a future time period such that varying trends may be displayed to the interested user, as exemplarily depicted in FIG. 7C.

Figure 7A:
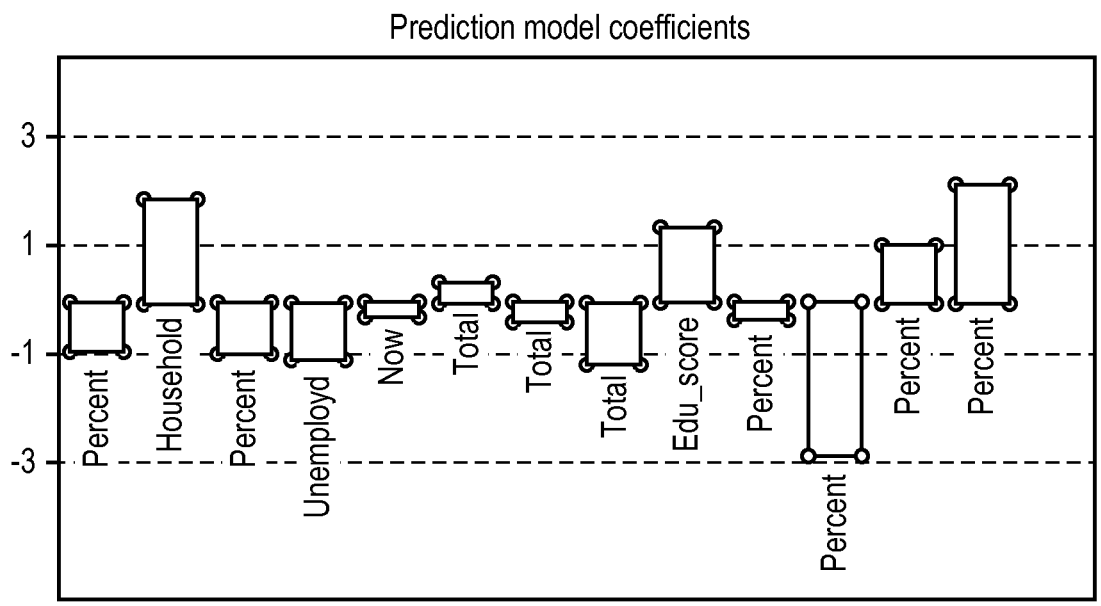
FIGS. 7A, 7B, and 7C respectively illustrate exemplary displays of learned coefficients of a regression model for each of a plurality of parameter values, a distribution of calculated statuses for a plurality of population segments, and status projections for three population segments, in accordance with one or more embodiments.

More particularly, on the X-axis of FIG. 7A is depicted a set of parameter values, and the coefficient weights of these parameter values are depicted on the Y-axis. The range from −3 to +3 is not intended to be limiting, as the weights may be in any suitable range. These weights may then be plugged into Eq. 1, described above. For example, weight $W_1$ may be −1 for parameter value $X_1$, the parameter value $X_1$ being in a category for percent of households with a male householder. A negative weight may represent an unimportant parameter value, e.g., which does not contribute heavily to the outcome. A large negative weight may signify that that parameter value is very unimportant. Similarly, a large positive weight may indicate that that parameter value is very important (e.g., the weight furthermost to the right in FIG. 7A). The opposite may also be true, namely that positive weights may indicate that that parameter value is unimportant and that negative weights may indicate that that parameter value is important.

Figure 7B:
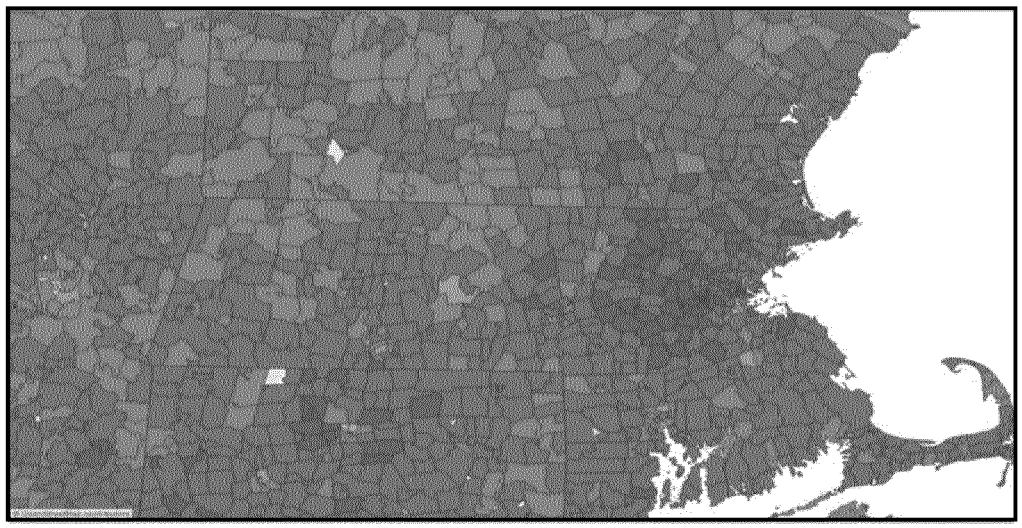

Further, FIG. 7B may represent statuses for population segments over a geographical area or map. But this is not intended to be limiting, as a distribution of the statuses may be represented in any other way. The intent of such a distribution may be to show comparative statuses of the respective population segments. In some embodiments, the distribution of FIG. 7B may be the outcomes of a prediction model and not the calculated statues.

Figure 7C:
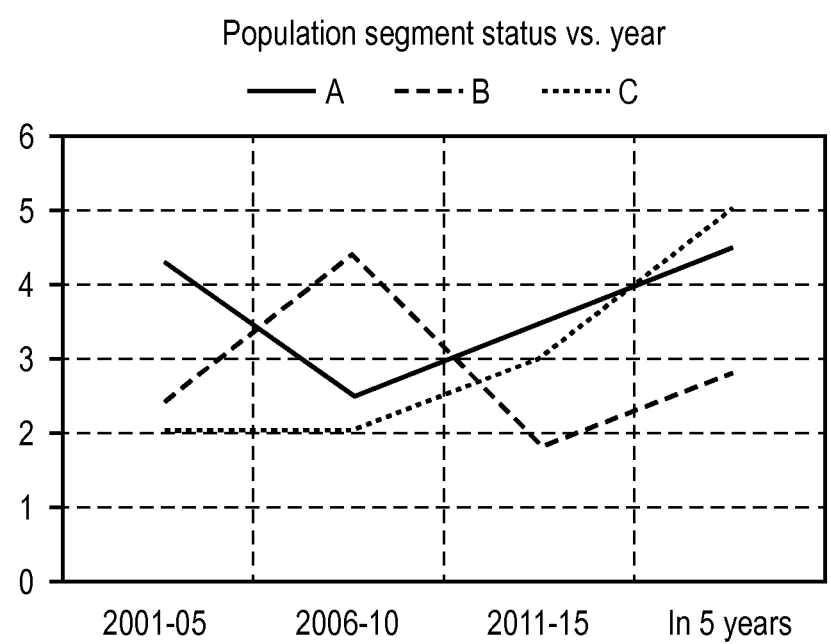

FIG. 7C depicts one example of the status plots of three population segments, in sequential time frames from 2001 to 2020. Evaluation component 38 may provide for display, though, any sequential or non-sequential time frames, for any number of population segments. The Y-axis may similarly hold any values, the status range from 0 to 6 of FIG. 7C not intended to be limiting.

In some embodiments, user interface device 18 may receive calculations, predictions, or other data from evaluation component 38. In these embodiments, user interface device 18 may be built as a web-based application with widely used front-end and back-end development techniques, such as HTML, JavaScript, Node.js, or other development technique. As such, users of system 10 may learn via user interface device 18 various facts of various population segments. For example, the users may better understand relationships between the received, calculated, and/or predicted socioeconomic parameter values, healthcare outcomes, and socioeconomic statuses.

Further, government or other officials, such as those associated with the Centers for Medicare & Medicaid Services (CMS), may consider the values, outcomes, and/or statuses received, calculated, and/or predicted by system 10 to fairly evaluate and adjust providers' performance As such, disenfranchised or underserved population segments may be better targeted by service providers, when certain values for the parameter values, outcomes, weights/coefficients, and/or statuses are identified. For example, healthcare providers may use the values, outcomes, and/or statuses received, calculated, and/or predicted to identify important socioeconomic determinants that largely impact the healthcare outcome. These healthcare providers may then arrange, e.g., transportation services to patients with limited access to transportation, if transportation availability is learned to be an important parameter, since it may have a large weight. Moreover, system 10's generated data may be used to do benchmarking on service providers that have similar underserved population segments to fairly compare the performance of the providers to improve overall the quality or outcome of provided services.

Figure 8:
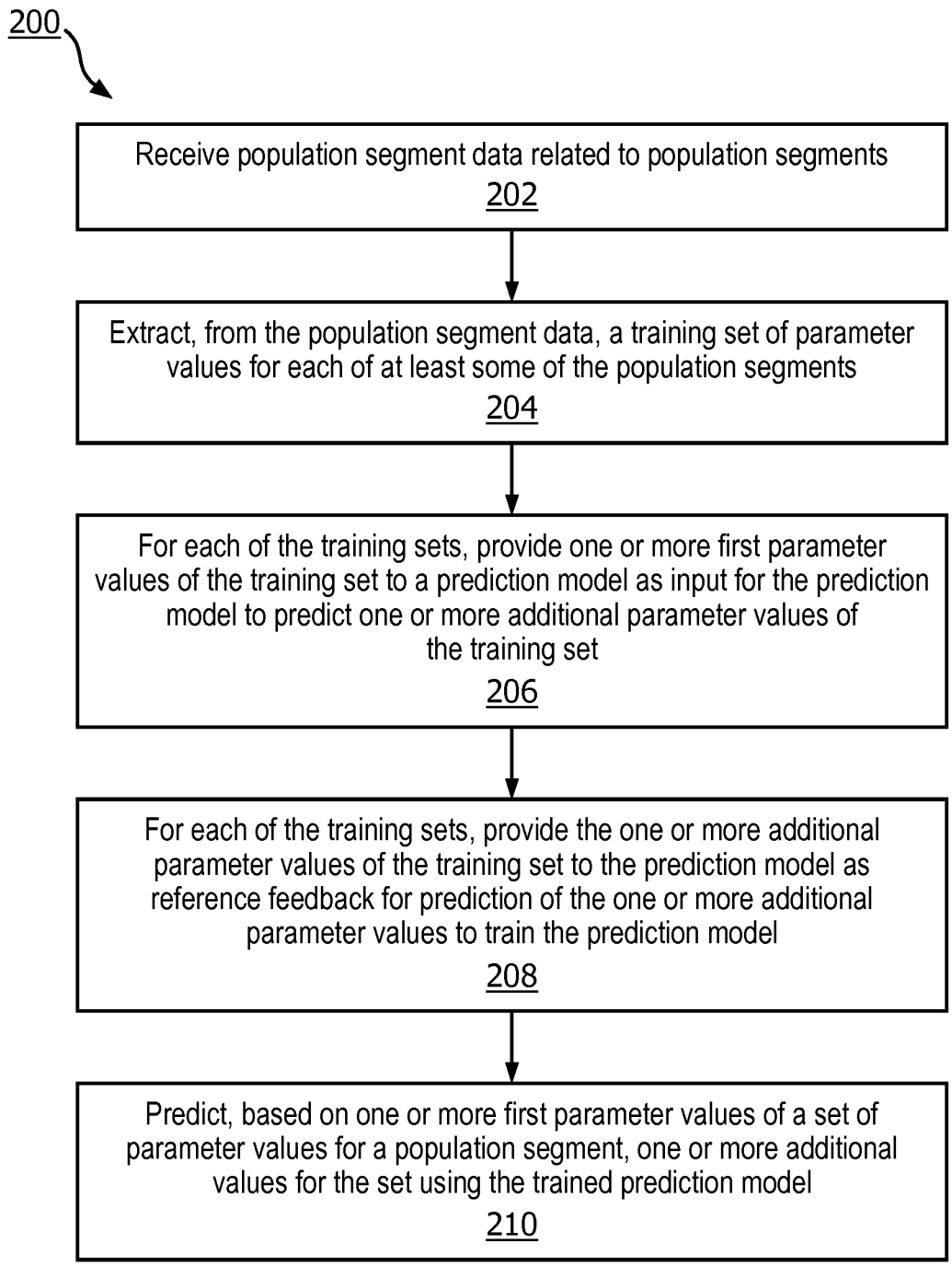
FIG. 8 illustrates a method for preparing and using one or more prediction models for socioeconomic data and missing value prediction, in accordance with one or more embodiments.

FIG. 8 illustrates a method for preparing and using one or more prediction models for socioeconomic data and missing value prediction, in accordance with one or more embodiments. Method 200 may be performed with a computer system comprising one or more computer processors and/or other components. The processors are configured by machine readable instructions to execute computer program components. The operations of method 200 presented below are intended to be illustrative. In some embodiments, method 200 may be accomplished with one or more additional operations not described, and/or without one or more of the operations discussed. Additionally, the order in which the operations of method 200 are illustrated in FIG. 8 and described below is not intended to be limiting.

In some embodiments, method 200 may be implemented in one or more processing devices (e.g., a digital processor, an analog processor, a digital circuit designed to process information, an analog circuit designed to process information, a state machine, and/or other mechanisms for electronically processing information). The processing devices may include one or more devices executing some or all of the operations of method 200 in response to instructions stored electronically on an electronic storage medium. The processing devices may include one or more devices configured through hardware, firmware, and/or software to be specifically designed for execution of one or more of the operations of method 200.

At operation 202 of method 200, population segment data related to one or more population segments may be received from one or more databases. As an example, the population segment data may include one or more sets of parameter values. In some embodiments, operation 202 is performed by a processor component the same as or similar to information component 30 (shown in FIG. 1 and described herein).

At operation 204, a training set of parameter values for each of at least some of the population segments may be extracted from the received population segment data. In some examples, each parameter value of the training set of parameter values may correspond to a socioeconomic category. In some use cases, some or all of the parameter values may be in different socioeconomic categories. In some embodiments, operation 204 is performed by a processor component the same as or similar to extraction component 32 (shown in FIG. 1 and described herein).

At operation 206, one or more extracted first parameter values of one or more training sets may be provided to a prediction model as input for the prediction model to predict one or more additional parameter values for at least some of the one or more training sets. In some embodiments, the prediction model may be provided, as input, first parameter values from each of the training sets. In some embodiments, the first parameter values may be provided such that the prediction of the one or more additional parameter values of the training set is performed by the prediction model without reliance on the one or more additional parameter values. In some embodiments, the prediction model used in operation 206 may be one of the prediction models described herein. In some embodiments, operation 206 is performed by a processor component the same as or similar to training component 34 (shown in FIG. 1 and described herein).

At operation 208, the one or more additional parameter values of the training set, for each of at least some of the training sets, may be provided to the prediction model as reference feedback for prediction of the one or more additional parameter values. The prediction model may utilize the reference feedback to train the prediction model. In some embodiments, the reference feedback may be known parameter values that are purposefully removed for the training of the prediction model. In some embodiments, operation 208 is performed by a processor component the same as or similar to training component 34 (shown in FIG. 1 and described herein).

At operation 210, one or more additional values of a set may be predicted for a population segment using the trained prediction model based on one or more first parameter values of the set. In some embodiments, the set of parameter values is a working set of parameter values. In some embodiments, operation 210 is performed by a processor component the same as or similar to prediction component 36 (shown in FIG. 1 and described herein).

Figure 9:
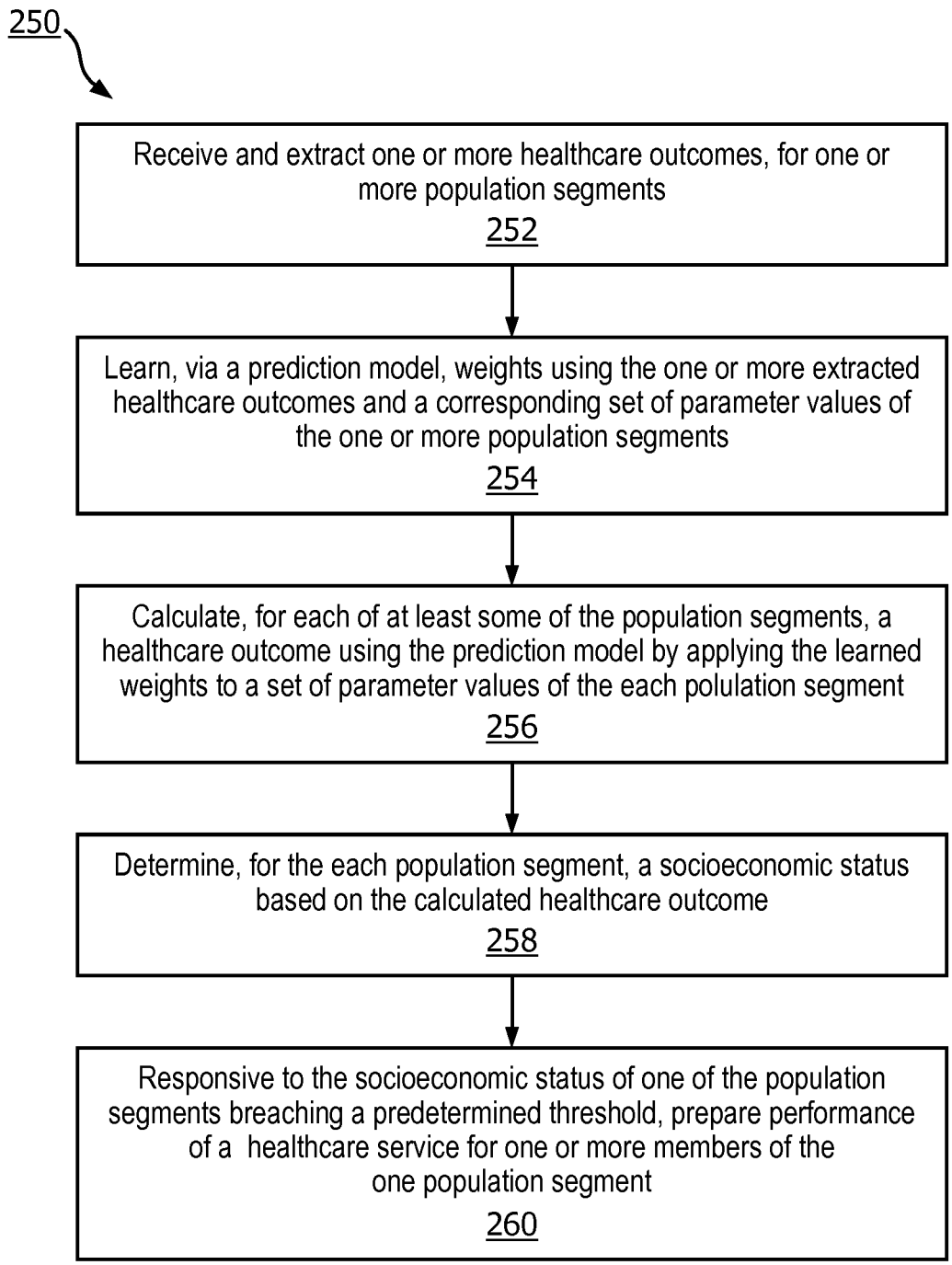
FIG. 9 illustrates a method for triggering a healthcare service responsive to a population segment's status being determined to be in need of remedy, in accordance with one or more embodiments.

FIG. 9 illustrates a method for triggering a healthcare service responsive to a population segment's status being determined to be in need of remedy, in accordance with one or more embodiments. Method 250 may be performed with a computer system comprising one or more computer processors and/or other components. The operations of method 250 presented below are intended to be illustrative. In some embodiments, method 250 may be accomplished with one or more additional operations not described, and/or without one or more of the operations discussed. Additionally, the order in which the operations of method 250 are illustrated in FIG. 9 and described below is not intended to be limiting.

In some embodiments, method 250 may be implemented in one or more processing devices. The processing devices may include one or more devices executing some or all of the operations of method 250 in response to instructions stored electronically on an electronic storage medium. The processing devices may include one or more devices configured through hardware, firmware, and/or software to be specifically designed for execution of one or more of the operations of method 250.

At operation 252, one or more outcomes may be received as part of received population segment data. The one or more outcomes may be received from one or more databases for one or more population segments. In some embodiments, the one or more databases from which the one or more healthcare outcomes are received may be different from the source(s) from which the parameter values is received, but in other embodiments the sources may be the same. In some embodiments, the outcomes may be healthcare outcomes. The one or more outcomes may be extracted from the received population segment data. In some embodiments, operation 252 is performed by a processor component the same as or similar to information component 30 and/or extraction component 32 (shown in FIG. 1 and described herein).

At operation 254, coefficient weights may be learned, via a prediction model, using the one or more received healthcare outcomes and one or more sets of parameters values of the one or more population segments. In some embodiments, the weights are learned using a similar regression model as the one listed in Eq. 1. In some embodiments, operation 254 is performed by a processor component the same as or similar to training component 34 (shown in FIG. 1 and described herein).

At operation 256, at least one healthcare outcome may be calculated, for each of at least some of the population segments, using the prediction model by applying the learned weights to a set of parameter values of the each population segment. By understanding how the different parameter values contribute, via the learned weights, to an outcome, evaluation component 38 may facilitate understanding of the relative importance of each parameter value.

In some embodiments, operation 256 is performed by a processor component the same as or similar to prediction component 36 (shown in FIG. 1 and described herein).

At operation 258, a status may be determined, for each of at least some population segments, based on the calculated outcome. For example, a healthcare status may be determined based on a calculated healthcare outcome or on an extracted healthcare outcome. In some embodiments, operation 258 is performed by a processor component the same as or similar to prediction component 36 or evaluation component 38 (shown in FIG. 1 and described herein).

At operation 260, responsive to a determined socioeconomic status of one of the population segments breaching a predetermined threshold, performance of a healthcare service may be prepared, for one or more members of the one population segment. In some embodiments, operation 260 is performed by a processor component the same as or similar to evaluation component 38 (shown in FIG. 1 and described herein).

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

What is claimed is:

1. A system for preparing and using one or more prediction models for socioeconomic data and missing value prediction, the system comprising one or more processors configured by machine-readable instructions to:
   receive, from one or more databases, population segment data related to a plurality of different population segments;
   extract, from the population segment data, a training set of parameter values for each of at least some of the plurality of different population segments, wherein each parameter value of the training set of parameter values corresponds to a socioeconomic category, and wherein at least some of the parameter values of the training set of parameter values correspond to different socioeconomic categories;
   for each training set of the training sets of parameter values, provide one or more first parameter values of the training set to a prediction model as input for the prediction model to predict one or more additional parameter values of the training set such that the prediction of the one or more additional parameter values of the training set is performed by the prediction model without reliance on the one or more additional parameter values;
   for each training set of the training sets of parameter values, provide the one or more additional parameter values of the training set to the prediction model as reference feedback for the prediction model's prediction of the one or more additional parameter values to train the prediction model;
   predict, based on one or more first parameter values of a set of parameter values for a population segment, one or more additional values for the set of parameter values using the prediction model subsequent to the training of the prediction model; and
   determining, using the population segment data and the one or more additional values for the set of parameter values as input to a trained outcome model, a health outcome or socioeconomic status for one or more of the plurality of different population segments.

2. The system of claim 1, wherein the one or more processors are configured by machine-readable instructions to train the prediction model by, for each training set of the training sets of parameter values:
   providing the one or more additional parameter values of the training set to the prediction model as reference feedback for the prediction model's prediction of the one or more additional parameter values; and
   performing, via the prediction model, a mean squared error (MSE) algorithm to minimize one or more differences between (i) the one or more additional parameter values provided as reference feedback and (ii) the prediction of the one or more additional parameter values.

3. The system of claim 1, wherein the one or more processors are configured by machine-readable instructions to, for each population segment of at least some of the plurality of different population segments:
   determine a healthcare outcome for the population segment using a second prediction model;
   determine a socioeconomic status for the population segment based on the healthcare outcome; and
   responsive to the socioeconomic status of the population segment breaching a predetermined threshold, prepare performance of a healthcare service for one or more members of the population segment.

4. The system of claim 3, wherein the second prediction model is used to calculate the healthcare outcome by applying learned weights to a set of parameter values of the each population segment, wherein the one or more processors are configured by machine-readable instructions to:
   extract, from the received population segment data, one or more healthcare outcomes; and
   learn, via the second prediction model, the weights using the one or more extracted healthcare outcomes and a set of parameters values of the each population segment.

5. The system of claim 3, wherein the second prediction model is a regression model.

6. The system of claim 1, wherein the one or more processors are configured by machine-readable instructions to:
   extract, from the population segment data, a working set of parameter values for each of at least some of the plurality of different population segments, wherein each parameter value of the working set of parameter values corresponds to a socioeconomic category;
   determine a set of similar population segments, the set of similar population segments including:

at least one of the population segments each lacking one or more second parameter values in the respective working set, and at least two of the population segments each having one or more third parameter values in the training set, wherein each of the one or more third parameter values is in a same socioeconomic category as one of the one or more second parameter values; and predict at least one of the one or more second parameter values based on an average of the third parameter values that are in the same socioeconomic category as the one of the one or more second parameter values.

7. The system of claim 1, wherein the one or more processors are configured by machine-readable instructions to:

train a machine learning model using one or more sets of parameter values and one or more socioeconomic statuses associated with each of at least one population segment; and predict, for the at least one population segment via the trained model, an additional socioeconomic status in a first time frame using at least one set of parameter values associated with the at least one population segment and at least one socioeconomic status associated with the at least one population segment in at least one second time frame.

8. A system for preparing and using one or more prediction models for socioeconomic data and missing value prediction, the system comprising:

means for receiving, from one or more databases, population segment data related to a plurality of different population segments;

means for extracting, from the population segment data, a training set of parameter values for each of at least some of the plurality of different population segments, wherein each parameter value of the training set of parameter values corresponds to a socioeconomic category, and wherein at least some of the parameter values of the training set of parameter values correspond to different socioeconomic categories;

means for providing, for each training set of the training sets of parameter values, one or more first parameter values of the training set to a prediction model as input for the prediction model to predict one or more additional parameter values of the training set such that the prediction of the one or more additional parameter values of the training set is performed by the prediction model without reliance on the one or more additional parameter values;

means for providing, for each training set of the training sets of parameter values, the one or more additional parameter values of the training set to the prediction model as reference feedback for the prediction model's prediction of the one or more additional parameter values to train the prediction model;

means for predicting, based on one or more first parameter values of a set of parameter values for a population segment, one or more additional values for the set of parameter values using the prediction model subsequent to the training of the prediction model; and means for determining, using the population segment data and the one or more additional values for the set of parameter values as input to a trained outcome model, a health outcome or socioeconomic status for one or more of the plurality of different population segments.

9. The system of claim 8, wherein the prediction model is trained by, for each training set of the training sets of parameter values:

providing the one or more additional parameter values of the training set to the prediction model as reference feedback for the prediction model's prediction of the one or more additional parameter values; and performing, via the prediction model, a mean squared error (MSE) algorithm to minimize one or more differences between (i) the one or more additional parameter values provided as reference feedback and (ii) the prediction of the one or more additional parameter values.

10. The system of claim 8, further comprising:

means for determining, for each population segment of at least some of the plurality of different population segments, a healthcare outcome for the population segment using a second prediction model;

means for determining, for the each population segment, a socioeconomic status for the population segment based on the healthcare outcome; and means for preparing, for the each population segment responsive to the socioeconomic status of the population segment breaching a predetermined threshold, performance of a healthcare service for one or more members of the population segment.

11. A method for preparing and using one or more prediction models for socioeconomic data and missing value prediction, the method being implemented by one or more processors configured by machine-readable instructions, the method comprising:

receiving, from one or more databases, population segment data related to a plurality of different population segments;

extracting, from the population segment data, a training set of parameter values for each of at least some of the plurality of different population segments, wherein each parameter value of the training set of parameter values corresponds to a socioeconomic category, and wherein at least some of the parameter values of the training set of parameter values correspond to different socioeconomic categories;

providing, for each training set of the training sets of parameter values, one or more first parameter values of the training set to a prediction model as input for the prediction model to predict one or more additional parameter values of the training set such that the prediction of the one or more additional parameter values of the training set is performed by the prediction model without reliance on the one or more additional parameter values;

providing, for each training set of the training sets of parameter values, the one or more additional parameter values of the training set to the prediction model as reference feedback for the prediction model's prediction of the one or more additional parameter values to train the prediction model; and predicting, based on one or more first parameter values of a set of parameter values for a population segment, one or more additional values for the set of parameter values using the prediction model subsequent to the training of the prediction model; and determining, using the population segment data and the one or more additional values for the set of parameter values as input to a trained outcome model, a health outcome or socioeconomic status for one or more of the plurality of different population segments.

12. The method of claim 11, wherein the one or more processors are configured by machine-readable instructions to train the prediction model by, for each training set of the training sets of parameter values:
   providing the one or more additional parameter values of the training set to the prediction model as reference feedback for the prediction model's prediction of the one or more additional parameter values; and
   performing, via the prediction model, a mean squared error (MSE) algorithm to minimize one or more differences between (i) the one or more additional parameter values provided as reference feedback and (ii) the prediction of the one or more additional parameter values.

13. The method of claim 11, wherein the one or more processors are configured by machine-readable instructions to, for each population segment of at least some of the plurality of different population segments:
   determine a healthcare outcome for the population segment using a second prediction model;
   determine a socioeconomic status for the population segment based on the healthcare outcome; and
   responsive to the socioeconomic status of the population segment breaching a predetermined threshold, prepare performance of a healthcare service for one or more members of the population segment.

14. The method of claim 13, wherein the second prediction model is used to calculate the healthcare outcome by applying learned weights to a set of parameter values of the each population segment,
   wherein the one or more processors are configured by machine-readable instructions to:
   extract, from the received population segment data, one or more healthcare outcomes; and
   learn, via the second prediction model, the weights using the one or more extracted healthcare outcomes and a set of parameters values of the each population segment.

15. The method of claim 13, wherein the second prediction model is a regression model.

16. The method of claim 11, wherein the one or more processors are configured by machine-readable instructions to:
   extract, from the population segment data, a working set of parameter values for each of at least some of the plurality of different population segments, wherein each parameter value of the working set of parameter values corresponds to a socioeconomic category;
   determine a set of similar population segments, the set of similar population segments including:
      at least one of the population segments each lacking one or more second parameter values in the respective working set, and at least two of the population segments each having one or more third parameter values in the training set, wherein each of the one or more third parameter values is in a same socioeconomic category as one of the one or more second parameter values; and
   predict at least one of the one or more second parameter values based on an average of the third parameter values that are in the same socioeconomic category as the one of the one or more second parameter values.

17. The method of claim 11, wherein the one or more processors are configured by machine-readable instructions to:
   train a machine learning model using one or more sets of parameter values and one or more socioeconomic statuses associated with each of at least one population segment; and
   predict, for the at least one population segment via the trained model, an additional socioeconomic status in a first time frame using at least one set of parameter values associated with the at least one population segment and at least one socioeconomic status associated with the at least one population segment in at least one second time frame.

18. The method of claim 11, further comprising the step of providing to a user, via a user interface, the determined health outcomes or socioeconomic statuses for each of the one or more of the plurality of different population segments.

19. The method of claim 18, wherein the determined health outcomes or socioeconomic statuses are displayed via the user interface as a heat map or a chart.

20. The method of claim 11, further comprising the steps of:
   predicting, using a trained longitudinal model, a future health outcome or socioeconomic status for one or more of the plurality of different population segments, wherein the determined health outcome or socioeconomic status for one or more of the plurality of different population segments are used as input for the trained longitudinal model; and
   providing, via a user interface, the predicted future health outcome or socioeconomic status for one or more of the plurality of different population segments.

* * * * *